United States Patent [19]

Hagen et al.

[11] Patent Number: 5,059,240
[45] Date of Patent: Oct. 22, 1991

[54] 2,3-SUBSTITUTED 1,8-NAPHTHYRIDINES, THEIR PREPARATION AND THEIR USE AS ANTIDOTES

[75] Inventors: Helmut Hagen, Frankenthal; Juergen Pfister, Speyer; Hans Ziegler, Mutterstadt; Bruno Wuerzer, Otterstadt; Karl-Otto Westphalen, Speyer, all of Fed. Rep. of Germany

[73] Assignee: BASF Aktiengesellschaft, Ludwigshafen, Fed. Rep. of Germany

[21] Appl. No.: 486,867

[22] Filed: Mar. 1, 1990

[30] Foreign Application Priority Data

Mar. 11, 1989 [DE] Fed. Rep. of Germany ....... 3907938

[51] Int. Cl.$^5$ .................... A01N 43/90; C07D 471/02
[52] U.S. Cl. ......................... 71/94; 546/122; 71/88; 71/90; 71/92; 71/95; 71/98; 71/109; 71/123
[58] Field of Search ............ 546/122; 71/98, 88, 71/94, 109; 544/127, 362

[56] References Cited

PUBLICATIONS

Tetrahedron Report Number 92, Heteroannelations with o-Amino-aldehydes, Caluwe, vol. 36, pp. 2359–2407 (1980).
1,8-Naphthyridines, Part II, Preparation and Some Reactions of 2-Substituted Derivatives, Hawes et al., J. Chem. Soc. (1967), pp. 1564–1568.

*Primary Examiner*—Allan J. Robinson
*Assistant Examiner*—B. Burn
*Attorney, Agent, or Firm*—Keil & Weinkauf

[57] ABSTRACT

2,3-substituted 1,8-naphthyridines of the general formula I

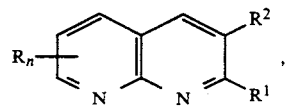

where:
R is hydrogen or $C_1$–$C_4$-alkyl (n=1 or 2)
$R^1$ is amino or substituted amino,
  $XR^5$, where X is oxygen or sulfur and $R^5$ is hydrogen, $C_1$–$C_{12}$-alkyl, $C_1$–$C_4$-alkoxycarbonyl-(($C_1$–$C_4$)-alkyl, $C_5$–$C_8$-cycloakyl, substituted or unsubstituted phenyl, substituted or unsubstituted phenyl-($C_1$–$C_3$)-alkyl,
  halogen,
  isothiorhonium halide,
  $C_1$–$C_{12}$-alkyl,
  $C_1$–$C_4$-alkoxycarbonyl-$C_1$–$C_4$-alkyl,
  substituted or unsubstituted phenyl or phenyl-($C_1$–$C_3$)-alkyl,
$R^2$ is $C_1$–$C_4$-alkyl, cyano, carboxyl or a group

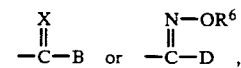

where
X is oxygen or sulfur,
B is $C_1$–$C_6$-alkyl, $C_1$–$C_6$-alkoxy or alkylthio, amino, mono- or dialkylamino, where each alkyl radical is of 1 to 4 carbon atoms, morpholino, piperidyl, chlorine, bromine or substituted or unsubstituted phenyl,
D is $C_1$–$C_4$alkyl or $NH_2$ and
$R^6$ is hydrogen, $C_1$–$C_8$-alkyl or alkylcarbonyl,
or $R^1$ and $R^2$ together are $-NH-N=C(CH_2)-$,
and their environmentally tolerated salts
with the proviso that $R^2$ is not cyano, carboxyl or a carboxamido or carboxylic ester group when $R^1$ is methyl, hydroxyl or amino ($NH_2$), processes for their manufacture, and herbicidal agents containing a naphthyridine I as safener and at least one herbicidal active ingredient selected from the group consisting of
a) 2-(4-heteroaryloxy)- or 2-(4-aryloxy)-phenoxyacetic acid derivatives and
b) cyclohexenone derivatives.

5 Claims, No Drawings

2,3-SUBSTITUTED 1,8-NAPHTHYRIDINES, THEIR PREPARATION AND THEIR USE AS ANTIDOTES

The present invention relates to 2,3-substituted 1,8-naphthyridines of the general formula I

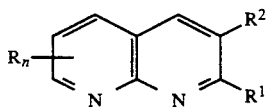

where

R is hydrogen or $C_1$–$C_4$-alkyl (n=1 or 2), $R^1$ is amino or $NR^3R^4$, in which $R^3$ is $C_1$–$C_{12}$-alkyl, $C_3$–$C_6$-alkenyl $C_3$–$C_8$-cycloalkyl, phenyl, phenyl-$C_1$–$C_3$-alkyl which can be substituted or monosubstituted to trisubstituted by halogen, $C_1$–$C_4$-alkyl, $C_1$–$C_4$-alkoxy, amino or mono- or dialkylamino where each alkyl radical is of 1 to 6 carbon atoms, or a group

where A is $C_1$–$C_8$-alkyl, $C_2$–$C_6$-alkenyl or phenyl which is unsubstituted or monosubstituted to trisubstituted by halogen and/or $C_1$–$C_4$-alkyl, or is amino, alkyl- or dialkylamino where each alkyl radical is of 1 to 6 carbon atoms, phenylamino, morpholino or piperidyl, and $R^4$ is hydrogen, $C_1$–$C_{12}$-alkyl or $C_3$–$C_8$-cycloalkyl, or $R^3$ and $R^4$ are bonded to one another to form a saturated or unsaturated 5-membered or 6-membered heterocyclic structure which, in addition to the nitrogen to which they are bonded, may contain a further heteroatom, such as oxygen or nitrogen;

hydrazino which is unsubstituted or monosubstituted or disubstituted by $C_1$–$C_4$-alkyl or monosubstituted by $C_1$–$C_4$-acyl;

$XR^5$, in which X is oxygen or sulfur and $R^5$ is hydrogen, $C_1$–$C_{12}$-alkyl, $C_1$–$C_4$-alkoxycarbonyl-$C_1$–$C_4$-alkyl, $C_5$–$C_8$-cycloalkyl, phenyl, phenyl-$C_1$–$C_3$-alkyl, phenyl or phenyl-$C_1$–$C_3$-alkyl, which are each substituted in the ring by halogen, $C_1$–$C_4$-alkyl, $C_1$–$C_4$-alkoxy, amino, mono- or dialkylamino where each alkyl radical is of 1 to 6 carbon atoms, halogen, isothiorhonium halide, $C_1$–$C_{12}$-alkyl, $C_1$–$C_4$-alkoxycarbonyl-$C_1$–$C_4$-alkyl, phenyl or phenyl-$C_1$–$C_3$-alkyl, where the aromatic radicals may carry from one to three of the following groups: halogen, $C_1$–$C_4$-alkyl, $C_1$–$C_4$ alkoxy, amino, nitro or mono- or dialkylamino where each alkyl radical is of 1 to 4 carbon atoms, $R^2$ is $C_1$–$C_4$-alkyl, cyano, carboxyl or a group

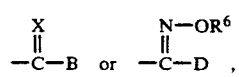

in which

X is oxygen or sulfur,

B is $C_1$–$C_6$-alkyl, $C_1$–$C_6$-alkoxy or alkylthio, amino, mono-or dialkylamino where each alkyl radical is of 1 to 4 carbon atoms, morpholino, piperidyl, chlorine, bromine or phenyl which in turn may carry from one to five halogen atoms and/or from one to three of the following groups: $C_1$–$C_4$-alkyl, $C_1$–$C_4$-alkoxy, $C_1$–$C_4$-haloalkyl, $C_1$–$C_4$-haloalkoxy and/or $C_1$–$C_4$-alkylthio;

D is $C_1$–$C_4$-alkyl or $NH_2$ and $R^6$ is hydrogen, $C_1$–$C_8$-alkyl or $C_2$–$C_8$-alkylcarbonyl, or $R^1$ and $R^2$ together are $-NH-N=C(NH_2)-$, and their plant-tolerated salts, with the proviso that when $R^1$ is methyl, hydroxyl or amino ($NH_2$), $R^2$ is not cyano, carboxyl or a carboxamido or carboxylic ester group.

The present invention furthermore relates to processes for the preparation of the compounds I and herbicides which contain 2-(4-hetaryloxy)- or 2-(4-aryloxy)-phenoxyacetic or -propionic acid derivatives and/or cyclohexenone derivatives as herbicidal active ingredients and 2,3-substituted 1,8-naphthyridines as antidotes, and methods for selectively controlling undesirable plant growth with these herbicides.

P. Caluwe describes the preparation of various 1,8-naphthyridine derivatives in Tetrahedron, 36 (1980), 2359–2407, in particular 2391–2394. 2-Amino-1,8-naphthyridines having carboxylic acid (derivative) radicals in the 3-position are disclosed in J. Chem. Soc. (C) (1967), 1564–1568. The prior art does not disclose any crop protection action of this class of compounds.

Herbicidal active ingredients from the group consisting of the 2-(4-hetaryloxy)- or 2-(4-aryloxy)-phenoxyacetic acid derivatives of the formula IV

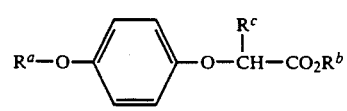

where $R^a$ is a phenyl ring, a pyridyl ring, a benzoxazyl radical, a benzothiazyl radical or a benzopyrazinyl radical, where these aromatic ring systems may carry up to two of the following radicals: halogen, $C_1$–$C_4$-alkyl, $C_1$–$C_4$-haloalkyl and/or nitro, $R^b$ is hydrogen, $C_1$–$C_4$-alkyl or one equivalent of a plant-tolerated cation and $R^c$ is hydrogen or methyl, are disclosed in the literature, for example in DE-A-22 23 984, DE-A-24 33 067, DE-A-25 76 251, DE-A-30 04 770, BE-A-868 875 and BE-A-858 618.

They are used for controlling undesirable plants from the gramineae family. However, the tolerance of these substances by crops varies between commercially acceptable and non-tolerated, depending on the substituents and application rate.

The same situation is encountered with cyclohexenone derivatives of the formula V

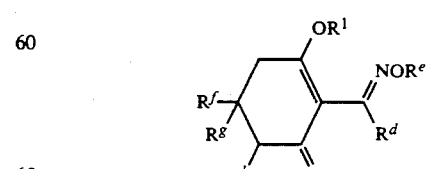

where $R^d$ is $C_1$–$C_4$-alkyl;

$R^e$ is $C_1$–$C_4$-alkyl, $C_3$- or $C_4$-alkenyl, $C_3$- or $C_4$-alkynyl, $C_3$-or $C_4$-haloalkylene or thenyl, which may be substituted by a halogen atom;

$R^f$ is $C_1$–$C_4$-alkyl which may be monosubstituted or disubstituted by $C_1$–$C_4$-alkylthio or $C_1$–$C_4$-alkoxy;

a 5-membered or 6-membered saturated or monounsaturated ring system which, in addition to carbon members, may contain an oxygen or sulfur atom or a sulfoxyl or sulfonyl group, and this ring system may carry up to three of the following radicals: hydroxyl, halogen, $C_1$–$C_4$-alkyl, $C_1$–$C_4$-haloalkyl, $C_1$–$C_4$-alkoxy and/or $C_1$–$C_4$-alkylthio;

a 10-membered saturated or monounsaturated heterocyclic structure which contains two oxygen atoms or sulfur atoms and may be substituted by up to three $C_1$–$C_4$-alkyl groups and/or methoxy groups;

phenyl, pyridyl, thiazolyl, pyrazolyl, pyrrolyl or isoxazolyl, where these groups may carry up to three of the following radicals: $C_1$–$C_4$-alkyl, $C_1$–$C_4$-haloalkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-dialkoxy-$C_1$–$C_3$-alkyl, formyl, halogen and/or benzoylamino;

$R^8$ is hydrogen, hydroxyl or, when $R^f$ is $C_1$–$C_6$-alkyl, a $C_1$–$C_6$-alkyl group;

$R^h$ is hydrogen, cyano, halogen, $C_1$–$C_4$-alkoxycarbonyl or a $C_1$–$C_4$-alkylketoxime and $R^i$ is hydrogen or one equivalent of an environmentally compatible cation.

They are described in the literature (for example EP-A 228 598, EP-A 230 235, EP-A 238 021, U.S. Pat. No. 4,432,786 and DE-A 24 39 104), likewise as herbicides, and are used predominantly for controlling undesirable grasses in dicotyledon crops and in grasses which do not belong to the gramineae family. Depending on the structure of the substituents and the dose used, compounds from this group can also be used for selectively controlling undesirable grasses in gramieous crops such as wheat and rice.

It is an object of the present invention to provide compounds which at least reduce the disadvantages encountered when using the abovementioned herbicides of the formula IV and V to such an extent that the herbicides are tolerated by the crops from the grass family.

We have found that this object is achieved by the 2,3-substituted 1,8-naphthyridines I defined at the outset. We have also found processes for the preparation of these compounds I and for the joint use of these compounds with the herbicides IV and V for influencing undesirable plant growth. The present invention furthermore relates to agents which contain the compounds I and the compounds excluded by the disclaimer, and whether the herbicidal active ingredient and the antidote are formulated and applied together or separately and, in the case of separate application, the order in which the herbicidal active ingredient and the antidote are applied are unimportant.

The novel compounds I are obtainable starting from o-aminopicolinaldehyde II, by reaction with a CH-acidic compound IIIa or IIIb.

The substitution pattern can be varied within a wide range by an appropriate choice of the CH-acidic compound III; in addition to acetyl and 1,3-dicarbonyl compounds, it is also possible to use β-ketoesters, acetonedicarboxylic esters, malonic esters, cyanoacetic esters and malodinitrile for the cyclodehydration.

The manufacture of compounds I is demonstrated with reference to the following reaction equations:

a) $R^1 \neq NH_2$, OH

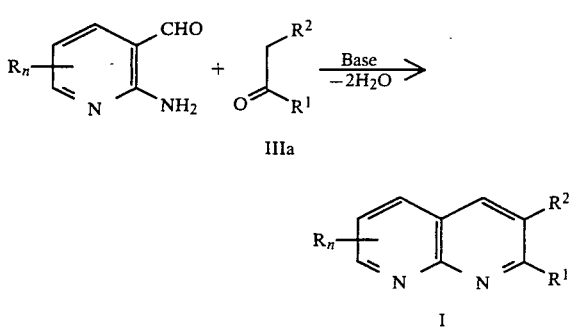

e.g. where
$R^1$ = OAlkyl, OAryl, $CH_2COOAlkyl$ or COOAlkyl,
$R^2$ = H, alkyl, alkylcarbonyl or COOAlky and
R = H or methyl b) $R^1 = NH_2$, OH

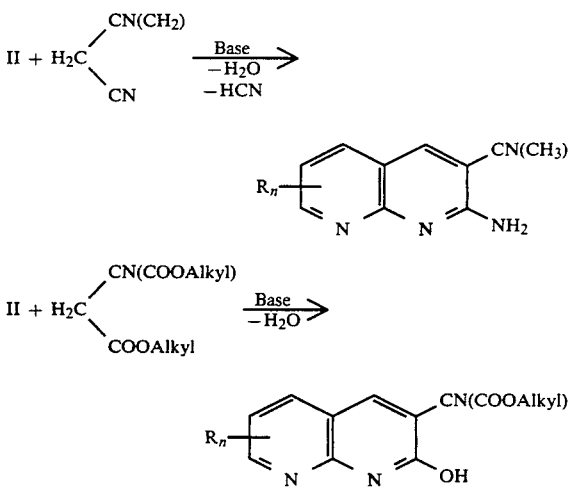

II + IIIb ⟶ I

2-Hydroxynaphthyridines react with a halogenating agent, such as phosphorus oxychloride or oxybromide to give 2-halonaphthyridines. The substitution pattern can be varied within a wide range by exchange reactions with N or S nucleophiles. In addition to primary and secondary amines, mercaptans, thioureas and thiocyanates are also suitable for this purpose (cf. for example The Chemistry of Heterocyclic Compounds, Volume 14, Part 1–5, E. Klingsberg, Ed., Interscience, New York/London, 1960 and Comprehensive Heterocyclic Chemistry, A. R. Katritzky, Ed., Pergamon Press 1984, Part 2, pp. 359–364.

Usually, the starting materials II and III are reacted in a stoichiometric ratio. However, an excess of one or other may be quite advantageous in specific cases.

The reaction can be carried out continuously or batchwise under atmospheric, superatmospheric or reduced pressure, using the conventional methods. The reaction temperature is in general from 20° to 2000° C., in particular from 50° to 150° C., advantageously in the region of the boiling point of the solvent.

Examples of solvents used are aliphatic and aromatic hydrocarbons and chlorohydrocarbons, such as petroleum ether, benzene, toluene, xylene, gasoline, dichloromethane, chloroform, tetrachloromethane, 1,2-dichloroethane or chlorobenzene, relatively high boiling ethers, such as tetrahydrofuran or dioxane, and nitriles, such as acetonitrile and propionitrile.

The bases used are, in particular, aliphatic, aromatic or heterocyclic amines, for example triethylamine, dimethylamine, diisopropylamine, piperidine, dimethylaniline, dimethylbenzylamine, pyridine and 4-dimethylaminopyridine, hydroxides of alkali and alkaline earth metals, e.g. sodium hydroxide, potassium hydroxide or calcium hydroxide, alcoholates of alkali and alkaline earth metals, e.g. sodium methylate, sodium ethylate, calcium methylate or potassium tert-butylate, and alkali or alkaline earth metal hydrides, e.g. sodium hydride, potassium hydride or calcium hydride.

In certain circumstances, it may be advantageous to carry out the condensation in the presence of a conventional phase transfer catalyst.

In view of the intended use of the compounds I as crop protection agents, the following radicals are suitable substituents:

R is hydrogen or $C_1-C_4$-alkyl, such as methyl, ethyl, propyl, isopropyl, butyl or isobutyl, preferably in the 5- and/or 7-position, n is 1 or 2, $R^1$ is amino or $NR^3R^4$, in which $R^3$ is $C_1-C_{12}$-alkyl, in particular $C_1-C_8$-alkyl, preferably $C_1-C_4$-alkyl, such as methyl, ethyl, propyl, isopropyl, n-butyl, sec-butyl, isobutyl or tert-butyl, $C_3-C_6$-alkenyl, such as allyl, 2-methylallyl or but-3-enyl, $C_3-C_8$-cycloalkyl, in particular cyclopentyl or cyclohexyl, phenyl which is unsubstituted or substituted by halogen, $C_1-C_4$-alkyl, $C_1-C_4$-alkoxy, amino or mono- or dialkylamino, such as methylamino, dimethylamino, ethylamino, diethylamino, propylamino, isopropylamino or tert-butylamino, phenyl-$C_1-C_3$-alkyl, such as benzyl or phenylethyl, where the phenyl nucleus may be substituted as stated above, a group

—C—A, where A is $C_2-C_6$ alkenyl, in particular $C_2-C_4$-alkenyl, such as ethenyl, prop-3-enyl or but-3-enyl, $C_1-C_8$-alkyl, in particular $C_1-C_4$-alkyl as stated for $R^3$, or phenyl which is unsubstituted or substituted by $C_1-C_4$-alkyl or halogen, such as fluorine, chlorine or bromine, or is amino, alkyl- or dialkylamino where each alkyl radical is of 1 to 6, in particular 1 to 4, carbon atoms, e.g. methylamino, dimethylamino, ethylamino, diethylamino, propylamino, dipropylamino, diisopropylamino, tert-butylamino or di-n-butylamino, or phenylamino, morpholino or piperidyl, $R^4$ is hydrogen, $C_1-C_{12}$-alkyl, in particular $C_1-C_8$-alkyl, preferably $C_1-C_4$-alkyl as stated for $R^3$, or $C_3-C_8$-cycloalkyl, e.g. cyclopentyl or cyclohexyl, or $R^3$ and $R^4$ are bonded to one another to form a saturated or unsaturated 5-membered or 6-membered heterocyclic structure which, in addition to the nitrogen to which they are bonded, may contain a further heteroatom, such as oxygen or nitrogen, for example to form a piperidyl, piperazinyl, morpholinyl, pyrrolidinyl, azolyl or imidazolyl ring, hydrazino which may be substituted by from one to three $C_1-C_4$-alkyl radicals, in particular by two geminal or vicinal $C_1-C_4$-alkyl radicals, e.g. methyl or ethyl, or may be monoacylated, a suitable acyl radical being $C_1-C_4$-acyl, in particular acetyl, $XR^5$, in which X is oxygen or sulfur and $R^5$ is hydrogen, $C_1-C_{12}$-alkyl as stated for $R^3$, $C_1-C_4$-alkoxycarbonyl-$C_1-C_4$-alkyl, such as $CH_2COOCH_3$ or $CH_2COOC_2H_5$, $C_5-C_8$-cycloalkyl as stated for $R^3$ or unsubstituted or substituted phenyl or phenyl-$C_1-C_3$-alkyl as stated under $R^3$, halogen, isothiorhonium halide

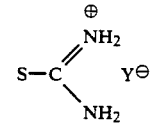

in which Y is fluorine, chlorine, bromine or iodine, in particular chlorine or bromine, $C_1-C_{12}$-alkyl as stated for $R^3$, $C_1-C_4$-alkoxycarbonyl-$C_1-C_4$-alkyl, in particular $C_1-C_3$-alkoxycarbonyl-$C_1$- or $-C_2$-alkyl, such as methoxycarbonylmethyl, ethoxycarbonylmethyl, 1-(methoxycarbonyl)-ethyl or 1-(ethoxycarbonyl)-ethyl, phenyl or phenyl-$C_1-C_3$-alkyl, such as benzyl or phenylethyl, where the phenyl nucleus in each case may be monosubstituted to trisubstituted in each case by halogen, $C_1-C_4$-alkyl, $C_1-C_4$-alkoxy, $NH_2$, $NO_2$ or mono- or dialkylamino where each alkyl radical is of 1 to 4 carbon atoms, $R^2$ is $C_1-C_4$-alkyl, such as methyl, ethyl, propyl, 1-methylethyl, butyl, 1-methylpropyl, 2-methylpropyl or 1,1-dimethylethyl, cyano, COOH, or a group

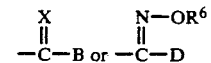

where

X is oxygen or sulfur,

B is $C_1-C_6$-alkoxy or $C_1-C_6$-alkylthio, such as methoxy, ethoxy, propoxy, isopropoxy, butoxy, methylthio, ethylthio, propylthio or butylthio, phenyl, amino, $C_1-C_4$-monoalkylamino, e.g. methylamino, ethylamino or propylamino, or $C_2-C_8$-dialkylamino, e.g. dimethylamino, diethylamino, dipropylamino or dibutylamino, morpholino, piperidyl, $C_1-C_6$-alkyl as stated for $R^3$, and n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 3,3-dimethylbutyl, 2,3-dimethylbutyl or 2-ethylbutyl, chlorine or bromine or phenyl which in turn may carry from 1 to 3 of the following groups: halogen, in particular fluorine, chlorine or bromine, alkyl, in particular methyl, ethyl or isopropyl, alkoxy, in particular methoxy, haloalkyl, in particular difluoromethyl, trifluoromethyl or chloromethyl, haloalkoxy, in particular difluoromethoxy or trifluoromethoxy and/or alkylthio, in particular methylthio or ethylthio, and D is $C_1-C_4$-alkyl as stated for $R^3$ or $NH_2$ and $R^6$ is hydrogen, $C_1-C_8$-alkyl as stated for $R^3$ or $C_1-C_8$-alkylcarbonyl, such as acetyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl, in particular acetyl, or $R^1$ and $R^2$ together form —NH—N=C(NH₂)—, and plant-tolerated salts of these compounds.

Specific examples of herbicidal hetaryloxy- or aryloxyphenoxyacetic acid derivatives of the formula IV whose toleration by crop plants can be improved by 2,3-subshtituted 1,8-naphthyridines of the formula I are listed in Table A below:

TABLE A $$R^a-O-\phantom{X}\!\!-O-\overset{R^c}{\underset{|}{CH}}-CO_2R^b \qquad IV$$

| Nr. | $R^a$ | $R^b$ | $R^c$ | Lit |
|---|---|---|---|---|
| IV.1 | 3,4-dichlorophenyl | CH₃ | CH₃ | DE-A 22 23 894 |
| IV.2 | 5-CF₃-pyridin-2-yl | n-C₄H₉ | CH₃ | BE-A 868 875 |

TABLE A-continued $$R^a-O-\phantom{X}\!\!-O-\overset{R^c}{\underset{|}{CH}}-CO_2R^b \qquad IV$$

| Nr. | $R^a$ | $R^b$ | $R^c$ | Lit |
|---|---|---|---|---|
| IV.3 | (isopropylideneamino)-(2-chlorophenyl) group | C₂H₅ | CH₃ | BE-A 858 618 |
| IV.4 | 3-CF₃-5-Cl-pyridin-2-yl | CH₃ | CH₃ | BE-A 868 875 |
| IV.5 | 6-Cl-quinoxalin-2-yl | C₂H₅ | CH₃ | DE-A 30 04 770 |

Specific examples of cyclohexenones of the formula V whose toleration by crop plants can be improved by 2,3-substituted 1,8-naphthyridines of the formula I are listed in Table B below.

TABLE B

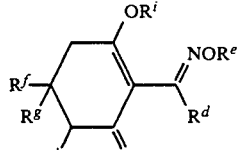

| No. | $R^d$ | $R^e$ | $R^f$ | $R^g$ | $R^h$ | $R^i$ | Literature |
|---|---|---|---|---|---|---|---|
| V.1 | C₃H₇ | CH₂CH=CH₂ | CH₃ | CH₃ | CO₂CH₃ | Na | DE-A 2 439 104 |
| V.2 | C₃H₇ | CH₂CH₃ | CH₂CH(CH₃)SCH₂CH₃ | H | H | H | DE-A 2 822 304 |
| V.3 | C₂H₅ | CH₂CH=CHCl | CH₂CH(CH₃)SCH₂CH₃ | H | H | H | US-A 4 440 566 |
| V.4 | C₃H₇ | CH₂CH=CHCl | CH₂CH(CH₃)SCH₂CH₃ | H | H | H | US-A 4 440 566 |
| V.5 | C₃H₇ | C₂H₅ | tetrahydrothiopyranyl | H | H | H | EP-A 71 707 |
| V.6 | C₂H₅ | C₂H₅ | tetrahydrothiopyranyl | H | H | H | EP-A 71 707 |
| V.7 | CH₃ | CH₂CH=CHCH₃ | tetrahydrothiopyranyl | H | H | H | EP-A 71 707 |
| V.8 | C₃H₇ | C₂H₅ | tetrahydropyranyl | H | H | H | EP-A 71 707 |
| V.9 | C₂H₅ | CH₂CH=CHCl | tetrahydropyranyl | H | H | H | EP-A 142 741 |

TABLE B-continued

V

Structure: cyclohexenone with $OR^i$, $=NOR^e$, $R^d$, $R^f$, $R^g$, $R^h$ substituents

| No. | $R^d$ | $R^e$ | $R^f$ | $R^g$ | $R^h$ | $R^i$ | Literature |
|---|---|---|---|---|---|---|---|
| V.10 | $C_3H_7$ | $C_2H_5$ | 2-pyridyl | H | H | H | EP-A 66 195 |
| V.11 | $C_2H_5$ | $C_2H_5$ | 4-methylphenyl | H | H | H | DE-A 24 39 104 |
| V.12 | $C_2H_5$ | $CH_2CH=CHCH_3$ | 4-ethylphenyl | H | H | H | DE-A 38 08 072 |
| V.13 | $C_2H_5$ | $C_2H_5$ | 2,4,6-trimethylphenyl | H | H | H | EP-A 88 301 |
| V.14 | $C_3H_7$ | $CH_2CH=CHCl$ | 4-methylcyclohexyl | H | H | H | EP-A 88 299 |
| V.15 | $C_3H_7$ | $CH_2CH=CHCH_3$ | 4-methylcyclohexyl | H | H | H | EP-A 88 299 |
| V.16 | $C_2H_5$ | $CH_2CH=CHCH_3$ | 3-isopropyl-5-methylisoxazol-4-yl | H | H | H | EP-A 238 021 |
| V.17 | $C_3H_7$ | $CH_2CH=CHCH_3$ | 3-isopropyl-5-methylisoxazol-4-yl | H | H | H | EP-A 238 021 |
| V.18 | $C_2H_5$ | $CH_2CH=CHCl$ | 4-(propargyloxy)phenyl | H | H | H | EP-A 137 174 |
| V.19 | $C_3H_7$ | $C_2H_5$ | 4-(ethoxymethyl)phenyl | H | H | H | EP-A 137 200 |
| V.20 | $C_3H_7$ | $C_2H_5$ | 3,4-dibromotetrahydropyran-4-yl | H | H | H | EP-A 230 235 |

TABLE B-continued $$V$$

Structure: cyclohexenone with $OR^i$, $=NOR^e$ (on substituent $R^d$), $R^f$, $R^g$, $R^h$ substituents, and a ketone (=O).

| No. | $R^d$ | $R^e$ | $R^f$ | $R^g$ | $R^h$ | $R^i$ | Literature |
|---|---|---|---|---|---|---|---|
| V.21 | $C_3H_7$ | $CH_2CH=CHCl$ | 3,4-dibromotetrahydropyran-4-yl (Br, Br on tetrahydropyran with methyl) | H | H | H | EP-A 230 235 |
| V.22 | $C_3H_7$ | $CH_2CH=CHCl$ | 2,6,6-trimethylcyclohex-1-en-1-yl ($H_3C$, $CH_3$, $CH_3$) | H | H | H | EP-A 46 860 |
| V.23 | $C_3H_7$ | $C_2H_5$ | cyclohexyl | H | H | H | JP-A 540 191 945 |
| V.24 | $C_3H_7$ | $C_2H_5$ | cyclohex-1-en-1-yl | H | H | H | EP-A 46 860 |
| V.25 | $CH_3$ | $CH_2CH=CHCl$ | 4-methylcyclohexyl ($CH_3$) | H | H | H | EP-A 88 299 |
| V.26 | $C_3H_7$ | $C_2H_5$ | 4-(trifluoromethyl)phenyl ($CF_3$) | H | H | K | EP-A 137 174 |
| V.27 | $C_2H_5$ | $CH_2CH=CHCl$ | 2,6,6-trimethylcyclohex-1-en-1-yl ($H_3C$, $H_3C$, $CH_3$) | H | H | H | EP-A 46 860 |
| V.28 | $C_3H_7$ | $CH_2CH=CHCH_3$ | 2-methyl-thiazol-4-yl (S, N, $CH_3$) | H | H | H | EP-A-125 094 |
| V.29 | $C_3H_7$ | $CH_2CH=CHCl$ | 2-methyl-thiazol-4-yl (S, N, $CH_3$) | H | H | H | EP-A-125 094 |
| V.30 | $C_3H_7$ | $C_2H_5$ | 2,4,6-trimethylphenyl ($H_3C$, $CH_3$, $CH_3$, $CH_3$) | H | H | H | EP-A-88 299 |

TABLE B-continued $$V$$

Structure: cyclohexane ring with $OR^i$, $R^f$, $R^g$, $R^h$ substituents and =C($R^d$)(NOR$^e$) group, with ketone (=O).

| No. | $R^d$ | $R^e$ | $R^f$ | $R^g$ | $R^h$ | $R^i$ | Literature |
|---|---|---|---|---|---|---|---|
| V.31 | C$_3$H$_7$ | CH$_2$CH=CH$_2$ | cyclohexyl with HO, H$_3$C, H$_5$C$_2$S substituents | H | H | H | EP-A-228 598 |
| V.32 | C$_2$H$_5$ | C$_2$H$_5$ | cyclohexyl with HO, HO substituents | H | H | H | EP-A-228 598 |
| V.33 | C$_3$H$_7$ | C$_2$H$_5$ | N-methylpyrazolyl | H | H | H | EP-A-66 195 |
| V.34 | C$_3$H$_7$ | CH$_2$CH=CHCl | N-methylpyrrolyl | H | H | H | EP-A-66 195 |
| V.35 | C$_3$H$_7$ | CH$_2$CH=CH$_2$ | 2-methyl-thiazoline | H | H | H | EP-A-125 094 |
| V.36 | C$_3$H$_7$ | C$_3$H$_7$ | CH(SCH$_2$CH$_3$)$_2$ | H | H | H | EP-A-230 260 |
| V.37 | C$_3$H$_7$ | C$_2$H$_5$ | tetrahydrothiopyranyl S-oxide | H | H | H | EP-A-115 808 |
| V.38 | C$_3$H$_7$ | C$_2$H$_5$ | tetrahydrothiopyranyl S,S-dioxide | H | H | H | EP-A-115 808 |
| V.39 | C$_3$H$_7$ | C$_3$H$_7$ | CH$_3$ | CH$_3$ | C(CH$_3$)=NOCH$_3$ | H | EP-A-172 551 |
| V.40 | C$_3$H$_7$ | CH$_2$CH=CH$_2$ | tetrahydrothiopyranyl S,S-dioxide | OH | H | H | Proceedings Brit. Crop Protection Conference - Weeds 1985, Vol.1, pp. 93-98 |

The herbicidal active ingredients and antidotes may be applied together or separately to the leaves and shoots of the crop plants and unwanted plants. Preferably, the antidote is applied together with the herbicidal active ingredient. If the components are applied separately, the antidote is applied first to the field and then the herbicidal active ingredient. The herbicidal active ingredient and antidote may be formulated together or separately as spray agents in the form of suspensions, emulsions or solutions.

Treatment of the crop plant seed with the antidote prior to sowing reduces the damage usually caused by the herbicide. The herbicidal active ingredient is then applied to the field on its own in conventional manner.

For herbicidal (heteroaryloxy)-phenoxyacetic acid derivatives, the amount of antidotally active compound varies, depending on the crop. The ratios may vary over a wide range, and are also dependent on the structure of the (heteroaryloxy)phenoxyacetic acid derivatives and on the crop involved. Suitable ratios of herbicidal active ingredient to antidote are from 1:4 to 1:10.01, and preferably from 1:4 to 1:0.1, parts by weight.

For the same cyclohexenone derivative, the amount of antidote varies, depending on the crop. The ratios in which a cyclohexenone derivative and a 1,8-naphthyridine derivative I are used may vary over a wide range, and are dependent on the structure of the cyclohexenone derivative, the naphthyridine derivative I and the crop involved. Suitable ratios of herbicidal active ingredient to safener are from 1:4 to 1:0.01, and preferably from 1:4 to 1:0.25, parts by weight.

The novel herbicidal agents may contain, in addition to the naphthyridine derivative I as safener and the herbicide from the group of the (heteroaryloxy)phenoxyacetic acids V, other herbicidal or growth-regulating active ingredients of different chemical structure without the safening effect being impaired.

The agents according to the invention, or—when applied separately—the herbicidal active ingredients and the safener, are applied for instance in the form of directly sprayable solutions, powders, suspensions (including high-percentage aqueous, oily or others), dispersions, emulsions, oil dispersions, pastes, dusts, broadcasting agents or granules by spraying, atomizing, dusting, broadcasting or pouring. The forms of application depend entirely on the purpose of which the active ingredients are to be used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredients and/or antidotes as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the herbicidal active ingredients and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably from 0.5 to 90, wt % of herbicidal active ingredient and antidote. The herbicidal active ingredient is applied at rates of from 0.1 to 2 kg/ha.

SYNTHESIS EXAMPLES

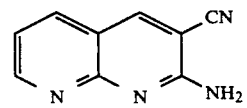

24.4 g (0.20 mol) of 2-aminonicotinaldehyde, 13.2 g (0.20 mol) of malonic dinitrile and 2 ml of piperidine were refluxed for 15 hours with 120 ml of ethanol. After cooling and suction filtration, the precipitate was washed with ethanol.

Yield: 23.0 g (85% of theory) or 2-amino-1,8-naphthyridine-3-carbonitrile of m.p. 260° C.

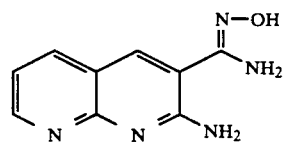

23.7 g (0.15 mol) of 2-amino-1,8-naphthyridine-3-carbonitrile, 14.0 g (0.20 mol) of hydroxylammonium chloride and 16.8 g (0.20 mol) of sodium bicarbonate were refluxed for 15 hours in 250 ml of ethanol/water (3:2). After cooling, the precipitate was filtered off and washed with n-propanol.

Yield: 22.3 g (69%) of 2-amino-1,8-naphthyridine-3-carboxamide oxime of m.p. 280° C.

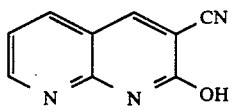

A mixture of 12.2 g (0.10 mol) of 2-aminonicotinaldehyde, 12.8 g (0.12 mol) ethyl cyanoacetate, 1 ml of pyridine and 200 ml of ethanol was refluxed to boiling for 30 minutes. After cooling, a precipitate formed which was isolated and purified in conventional manner.

Yield: 13.6 g 80.5% of theory) of 3-cyano-2-hydroxy-1,8-naphthyridine of m.p. >240° C.

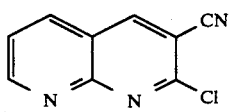

A mixture of 17.1 g (0.1 mol) of 3-cyano-2-hydroxyl-1,8-naphthyridine and 50 ml of phosphorus oxychloride was heated for 3 hours at 100° C. After cooling, the reaction mixture was stirred into water. The aqueous mixture was made alkaline, as a result of which a precipitate was formed which was isolated and purified in conventional manner.

Yield: 15.5 g (82%) of 2-chloro-3-cyano-1,8-naphthyridine of m.p. >240° C.

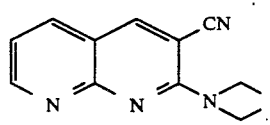

A mixture of 11.4 g (0.06 mol) of 2-chloro-2-cyano-1,8-naphthyridine, 15.4 ml (0.15 mol) of diethylamine and 100 ml of ethanol was refluxed to boiling for 6 hours. The reaction mixture was filtered hot and water was added to the solution thus obtained. After cooling a precipitate formed which was isolated and purified in conventional manner.

Yield: 10.3 g (76% of theory) of 3-cyano-2-(N,N-diethylamino)-1,8-naphthyridine of m.p. 119°–121° C.

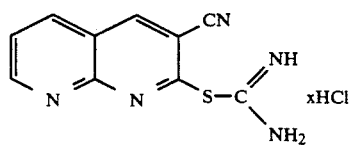

A mixturer of 19 g (0.1 mol) of 2-chloro-3-cyano-1,8-naphthyridine, 7.6 g (0.1 mol) of thiourea and 200 ml of ethanol was heated for 1 hour at 60° C. After cooling a precipitate formed which was isolated and purified in conventional manner.

Yield: 25.1 g (94% of theory) of 3-cyano-2-isothiuronio-1,8-naphthyridine hydrochloride of m.p. >240° C.

TABLE C 2,3-substituted 1,8-naphthyridines

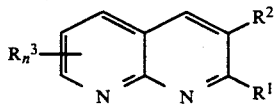

(I)

| Example No. | R$^1$ | R$^2$ | R$_n^3$ | Phys. data mp (°C.) or lit.$^{a)}$ |
|---|---|---|---|---|
| 1 | NH$_2$ | CN | H | (1), (2) |
| 2 | NHC$_2$H$_5$ | CN | H | |
| 3 | NHCH$_3$ | CN | H | |
| 4 | N(C$_2$H$_5$)$_2$ | CN | H | 119–121 |
| 5 | NHCOC$_2$H$_5$ | CN | H | 221–223 |
| 6 | NHCH$_2$CH=CH$_2$ | CN | H | 182–184 |
| 7 | NHCOCH$_3$ | CN | H | 200–205 |
| 8 | NHCONHCH$_3$ | CN | H | >240 |
| 9 | NHCONH-n-C$_4$H$_9$ | CN | H | 156–160 |
| 10 | NHCONHC$_6$H$_5$ | CN | H | 195 |
| 11 | morpholino | CN | H | 194–196 |
| 12 | OH | CN | H | (2) |
| 13 | S—C=NH$_2$⊕Cl⊖<br>\|<br>NH$_2$ | CN | H | >240 |
| 14 | Cl | CN | H | >240 |
| 15 | NH$_2$ | COOH | H | (1) |
| 16 | OH | COOH | H | (2) |
| 17 | CH$_2$COCH$_3$<br>\|\|<br>O | COOCH$_3$ | H | 126–130 |
| 18 | OH | COOC$_2$H$_5$ | H | 203–205 |
| 19 | N(C$_2$H$_5$)$_2$ | COOC$_2$H$_5$ | H | |
| 20 | S—C$_{12}$H$_{25}$ | COOC$_2$H$_5$ | H | oil |
| 21 | S—C(NH$_2$)=NH$_2$⊕Cl⊖ | COOC$_2$H$_5$ | H | 189 (decomp.) |
| 22 | Cl | COOC$_2$H$_5$ | H | 127–129 |
| 23 | CH$_3$ | COOC$_2$H$_5$ | H | 86–88 |
| 24 | NH$_2$ | CONH$_2$ | H | (2) |

TABLE C-continued

2,3-substituted 1,8-naphthyridines $$\text{(I)}$$

| Example No. | $R^1$ | $R^2$ | $R_n^3$ | Phys. data mp (°C.) or lit.[a] |
|---|---|---|---|---|
| 25 | $CH_3$ | CO—N(morpholino) | H | 155–158 |
| 26 | $NH_2$ | C(NH₂)=N—OH | H | 280 (decomp.) |
| 27 | $NH_2$ | CS—$NH_2$ | H |  |
| 28 | $CH_3$ | $COCH_3$ | H | 129–133 |
| 29 | $CH_3$ | C(CH₃)=N—OH | H | 176–178 |
| 30 | $CH_3$ | C(CH₃)=N—OC(O)CH₃ | H | 155–159 |
| 31 | $CH_3$ | $CH_3$ | H | 132–133 |
| 32 | $CH_3$ | CONH—(2-methoxyphenyl) | H | 246–248 |
| 33 | $CH_3$ | CONH—(4-chlorophenyl) | H | 172–173 |
| 34 | $NHCONHCH_2CH_3$ | CN | H | >250 |
| 35 | $N(COC_6H_5)_2$ | CN | H | 192–194 |
| 36 | $NH-C_6H_5$ | $CONH_2$ | H | >240 |
| 37 | $NH-C_6H_5$ | CN | H | >240 |
| 38 | $NH-CH_2C_6H_5$ | $CONH_2$ | H | 250–252 |
| 39 | $NH-(CH_2)_3CH_3$ | $CONH_2$ | H | 217–219 |
| 40 | 4-methylpiperazin-1-yl | CN | H | 145–148 |
| 41 | $NHNH-C_6H_5$ | CN | H | 174–176 |
| 42 | $OCH_3$ | CN | H | 202–204 |
| 43 | $S(CH_2)_3CH_3$ | CN | H | 92–94 |
| 44 | $SCH(CH_3)_2$ | CN | H | 113–114 |
| 45 | $SC(CH_3)_3$ | CN | H | 194–195 |
| 46 | —NH—N=C($NH_2$)— | | H | >240 |
| 47 | $NH_2$ | CN | 4,6-$(CH_3)_2$ | >300 |
| 48 | $NO_2$ | CN | H | >220 |
| | NH—(2,4-dinitro-6-trifluoromethylphenyl) | | | |

TABLE C-continued

2,3-substituted 1,8-naphthyridines

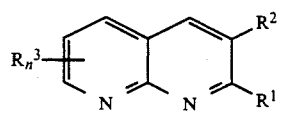

| Example No. | R¹ | R² | $R_n^3$ | Phys. data mp (°C.) or lit.[a] |
|---|---|---|---|---|
| 49 | NO₂ ... NH—(Ar)—CF₃ ... O₂N | CN | H | >220 |
| 50 | (CH₂)₂CH₃ | CH₂CH₃ | H | $bp_1$ = 130–135 |

[a] Literature:
(1) D. K. J. Gorecki, E. M. Hawes: J. Mech. Chem. 20 (1977) 124
(2) E. M. Hawes, D. G. Wibberley: J. Chem. Soc. C 1967, 1564
(3) K. R. Reddy, K. Mogilaiah, B. Screenivasulu, J. Ind. Chem. Soc. 64 (1987) 193)

EXAMPLES DEMONSTRATING BIOLOGICAL ACTION

The influence of various representatives of the herbicidal agents, or combinations of herbicide and antidote, according to the invention on the growth of unwanted and crop plants compared with the herbicidal active ingredient along is illustrated in the following greenhouse experiments.

The vessels employed were plastic flowerpots having a volume of 300 cm³ and filled with a sandy loam containing about 3.0% humus. The seeds of the test plants are sown separately, according to species, and then moistened. The vessels were then covered with transparent plastic hoods until the plants had taken root.

For the postemergence treatment, the plants were grown, depending on growth form, to a height of 3 to 20 cm before being treated with the active ingredients, which were suspended or emulsified in water and sprayed through finely distributing nozzles.

Where the safeners were used as seed dressings, a certain amount, e.g., 1 g, of active ingredient was applied per kg of seed. The seeds were then sown in the test vessels described above and grown to a height of from 3 to 5 cm before being treated with the herbicidal compounds. The plants were treated with the herbicidal compounds as described above.

As herbicidal active ingredient, the cyclohexenone derivative V.2 was used in the biological experiments.

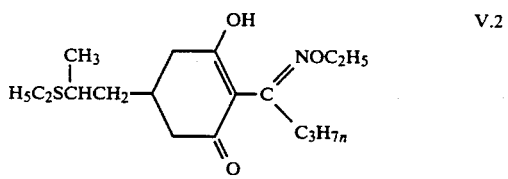

V.2

The herbicidal active ingredient V.2 was used (on its own and together with the safener) in the spray liquor as a commercially formulated product (184 g/l EC) together with the same amounts of solvent system XXII given in the table for the safener.

For the postemergence treatment, all the safeners were formulated in a mixture consisting of 80% of cyclohexenone and 20% of Emulphor EL (formulation XXII) with 10 wt % of active ingredient.

For seed treatment, the safener was formulated as a dust containing 40 wt % of active ingredient and a small amount of an adherent.

The test plants employed were *Avena fatua, Hordeum vulgare, Lolium multiflorum, Oryza sativa, Sorghum, Triticum aestivum* and *Zea mays*.

The vessles were set up in the greenhouse, heat-loving species at from 18° to 30° C. and species from more moderate climates at from 10° to 25° C.

The experiments were run for from 3 to 5 weeks. During this period, the plants were tended and their reactions to the various treatments assessed.

Damage by the chemical agents was assessed on a scale from 0 to 100% compared with the untreated control plants, 0 denoting no damage and 100 denoting complete destruction of the plants.

The tables below document the safening action of compound no. 1 according to the invention in foliage and seed treatment of crop plants, and of compounds nos. 18, 24 and 44 on postemergence (foliage) treatment. These compounds significantly improve the tolerance of the herbicide V.2 by wheat, rice and Indian corn.

TABLE 1

Improvement of the tolerance of the herbicide sethoxydim by wheat by admixing the safener compound no. 1 and applying postemergence in the greenhouse

| Appl. rate [kg/ha] | | Test plants and damage in % | |
|---|---|---|---|
| Herbicidal act. ingr. V.2 | Safener 1 | Crop plant *Triticum aestivum*[*] | Unwanted plant *Avena fatua* |
| 0.03 | — | 45 | 100 |
| 0.06 | — | 94 | 100 |
| 0.03 | 0.125 | 12 | 95 |
| 0.06 | 0.25 | 15 | 100 |

[*]Varieties: "Kanzler", "Okapi"

TABLE 2

Further example for the reduction of the phytotoxicity of the herbicide V.2 in wheat by admixing safener no. 24 and applying postemergence in the greenhouse

| Appl. rate [kg/ha] | | Test plants and damage in % | |
|---|---|---|---|
| Herbicidal act. ingr. V.2 | Safener 24 | Crop plant *Triticum aestivum*\* | Unwanted plant *Lolium multifl.* |
| 0.015 | — | 30 | 100 |
| 0.03 | — | 65 | 100 |
| 0.06 | — | 90 | 100 |
| 0.015 | 0.06 | 0 | 90 |
| 0.03 | 0.125 | 0 | 100 |
| 0.06 | 0.25 | 35 | 100 |

\*Variety: "Okapi"

TABLE 3

Protection of crop plants against the phytotoxicity of the herbicide V.2 by seed treatment with the safener compound no. 1

| Herbicidal act. ingr. V.2 Appl. rate [kg/ha] | Safener compound no. 1 Appl. rate [g/kg seed] | Damage in % in *Zea mays*\* [Indian corn] |
|---|---|---|
| 0.03 | — | 30 |
| 0.06 | — | 65 |
| 0.03 | 1 | 0 |
| 0.06 | 1 | 20 |

\*Variety: "Inrakorn"

TABLE 4

Improvement in the tolerance of the herbicide V.2 by wheat by joint application (mixture) with safener compound no. 44 on postemergence application in the greenhouse

| Appl. rate [kg/ha] | | Damage [%] | |
|---|---|---|---|
| Herbicidal act. ingr. V.2 | Safener compound 44 | *Triticum aestivum* | *Lolium multiflorum* |
| 0.03 | — | 70 | 98 |
| 0.03 | 0.125 | 25 | 90 |

\*Variety: "Star"

TABLE 5

Improvement of the tolerance of the herbicide V.2 by rice by joint application (mixture) with safener no. 18 on postemergence application in the greenhouse

| Appl. rate [kg/ha] | | Damage [%] | |
|---|---|---|---|
| Herbicidal act. ingr. V.2 | Safener compound 18 | *Oryza sativa*\* | *Echinochloa crus-galli* |
| 0.03 | — | 50 | 90 |
| 0.03 | 0.015 | 10 | 90 |

\*Variety: "Bahia"

We claim:

1. A herbicidal composition containing as antidote at least one 2,3-substituted 1,8-naphthyridine of the formula I

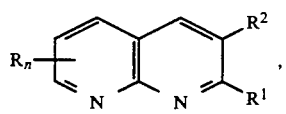

where:
R is hydrogen or $C_1$-$C_4$-alkyl (n=1 or 2)
$R^1$ is amino or $NR^3R^4$, in which
  $R^3$ is $C_1$-$C_{12}$-alkyl, $C_3$-$C_6$-alkenyl, $C_3$-$C_8$-cycloalkyl, phenyl, phenyl-($C_1$-$C_3$)-alkyl, or phenyl or phenyl-($C_1$-$C_3$)-alkyl mono- to trisubstituted by halogen, $C_1$-$C_4$-alkyl, $C_1$-$C_4$-alkoxy, $C_1$-$C_4$-haloalkyl, nitro, amino or mono- or dialkylamino where each alkyl radical is of 1 to 6 carbon atoms, or a group

where A is $C_1$-$C_8$-alkyl, $C_2$-$C_6$-alkenyl or phenyl which is unsubstituted or mono- or trisubstituted by halogen and/or $C_1$-$C_4$-alkyl, or is amino, alkyl- or dialkylamino where each alkyl radical is of 1 to 6 carbon atoms, or phenylamino, and $R^4$ is hydrogen, $C_1$-$C_{12}$-alkyl or $C_3$-$C_8$-cycloalkyl;
hydrazino which is unsubstituted or mono- or disubstituted by $C_1$-$C_4$-alkyl or monosubstituted by $C_1$-$C_4$-acyl;
$XR^5$, in which X is oxygen or sulfur and $R^5$ is hydrogen, $C_1$-$C_{12}$-alkyl, $C_1$-$C_4$-alkoxycarbonyl-($C_1$-$C_4$)-alkyl, $C_5$-$C_8$-cycloalkyl, phenyl, phenyl-$C_1$-$C_3$-alkyl, or phenyl or phenyl-$C_1$-$C_3$-alkyl, each of which is substituted in the ring by halogen, $C_1$-$C_4$-alkyl, $C_1$-$C_4$-alkoxy, amino, mono- or dialkylamino where each alkyl radical is of 1 to 6 carbon atoms,
halogen,
isothiorhonium halide,
$C_1$-$C_{12}$-alkyl,
$C_1$-$C_4$-alkoxycarbonyl-$C_1$-$C_4$-alkyl, phenyl or phenyl-($C_1$-$C_3$)-alkyl, where the aromatic radicals may carry from one to three of the following groups: halogen, $C_1$-$C_4$-alkyl, $C_1$-$C_4$-alkoxy, amino, nitro or mono- or dialkylamino where each alkyl radical is of 1 to 4 carbon atoms,
$R^2$ is $C_1$-$C_4$-alkyl, cyano, or a group

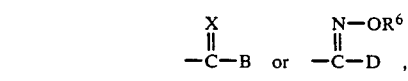

in which X is oxygen or sulfur,
  B is $C_1$-$C_6$-alkyl, $C_1$-$C_6$-alkoxy or alkylthio, amino, mono- or dialkylamino where each alkyl radical is of 1 to 3 carbon atoms, chlorine, bromine or phenyl, which in turn may carry from one to five halogen atoms and/or from one to three of the following groups: $C_1$-$C_4$-alkyl, $C_1$-$C_4$-alkoxy, $C_1$-$C_4$-haloalkyl, $C_1$-$C_4$-haloalkoxy and/or $C_1$-$C_4$-alkylthio;
  D is $C_1$-$C_4$-alkyl or $NH_2$ and
  $R^6$ is hydrogen, $C^1$-$C^8$-alkyl or $C_2$-$C_8$-alkylcarbonyl,
  or $R^1$ and $R^2$ together are $-NH-N=C(NH_2)-$,
or a plant-tolerated salt thereof,
and at least one herbicidal active ingredient selected from the group consisting of cyclohexenone derivatives of the formula V

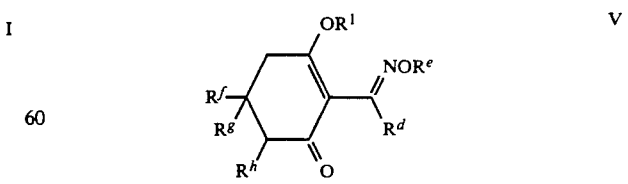

where:
$R^d$ is $C_1$-$C_4$-alkyl;
$R^e$ is $C_1$-$C_4$-alkyl, $C_3$-$C_4$-alkenyl, $C_3$-$C_4$-alkynyl, $C_3$-$C_4$-haloalkylene or thenyl which may be substituted by a halogen atom;

$R^f$ is

- $C_1$–$C_4$-alkyl which may be mono- or disubstituted by $C_1$–$C_4$-alkylthio or $C_1$–$C_4$-alkoxy;
- a 5- or 6-membered saturated or monounsaturated ring system which, in addition to carbon members, may contain an oxygen or sulfur atom or a sulfoxyl or sulfonyl group, and this ring system may carry up to three of the following radicals: hydroxy, halogen, $C_1$–$C_4$-alkoxy and/or $C_1$–$C_4$-alkylthio;
- a 10-membered saturated or monounsaturated heterocyclic structure which contains two oxygen atoms or sulfur atoms and may be substituted by up to three $C_1$–$C_4$-alkyl groups and/or methoxy groups;
- phenyl, pyridyl, thiazolyl, pyrazolyl, pyrrolyl or isoxazolyl, where these groups may carry up to three of the following radicals: $C_1$–$C_4$-alkyl, $C_1$–$C_4$-haloalkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy, $C_1$–$C_3$-alkyl, $C_1$–$C_4$-dialkoxy-$C_1$–$C_3$-alkyl, formyl, halogen and/or benzoylamino;

2. A herbicidal composition as described in claim 1, wherein the weight ratio between the antidote and the herbicidal active ingredient is from 0.01:1 to 4:1.

3. A process for the selective control of unwanted plants, wherein a 2,3-substituted 1,8-naphthyridine of the formula I as set forth in claim 1 and a cyclohexenone derivative as set forth in claim 1 are applied—simultaneously or one after the other in any order—before, during or after sowing of the crop plants or before or during emergence of the crop plants.

4. A process for preventing damage to crop plants by herbicidal cyclohexenone derivatives as set forth in claim 1 wherein the seed of the crop plants is treated with an antagonistically effective amount of a 2,3-substituted, 1,8-naphthyridine of the formula I as set forth in claim 1.

5. A process for the selective control of unwanted plants, wherein the leaves of the crop plants and the unwanted plants are treated post-emergence and either simultaneously or one after the other with a 2,3-substituted 1,8-naphthyridine of the formula I as set forth in claim 1 and with a cyclohexenone derivative of the formula V as set forth in claim 1.

* * * * *

UNITED STATES PATENT AND TRADEMARK OFFICE
CERTIFICATE OF CORRECTION

PATENT NO. : 5,059,240

DATED : Oct. 22, 1991.

INVENTOR(S) : Hagen et al

It is certified that error appears in the above-identified patent and that said Letters Patent is hereby corrected as shown below:

Claim 1, column 24, line 9, between "mono-" and "trisubstituted", delete "or" and sunstitute therefore --to--.

Claim 1, the chemical structure (formula V) between lines 55 and 63, should read --

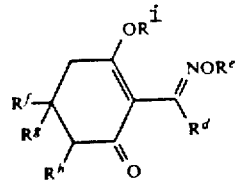

--

UNITED STATES PATENT AND TRADEMARK OFFICE
CERTIFICATE OF CORRECTION

PATENT NO. : 5,059,240
DATED : Oct. 22, 1991
INVENTOR(S) : Hagen et al.

It is certified that error appears in the above-identified patent and that said Letters Patent is hereby corrected as shown below:

Claim 1, immediately below "halogen and/or benzoylamino" on line 24 of column 25, insert -- $R^g$ is hydrogen, hydroxy or, when $R^f$ is $C_1$-$C_6$-alkyl, a $C_1$-$C_6$-alkyl group;

$R^h$ is hydrogen, cyano, halogen, $C_1$-$C_4$-alkoxycarbonyl or a $C_1$-$C_4$-alkylketoxime and $R^i$ is hydrogen or one equivalent of an environmentally compatible cation. --

Signed and Sealed this

Twenty-first Day of September, 1993

Attest:

BRUCE LEHMAN

*Attesting Officer*

*Commissioner of Patents and Trademarks*